United States Patent [19]
Federowicz et al.

[11] Patent Number: 5,700,828
[45] Date of Patent: Dec. 23, 1997

[54] TREATMENT OR PREVENTION OF ANOXIC OR ISCHEMIC BRAIN INJURY WITH MELATONIN-CONTAINING COMPOSITIONS

[75] Inventors: Michael G. Federowicz, Riverside, Calif.; Gregory M. Fahy, Gaithersburg, Md.; Lawrence E. Wood, Wrightwood, Calif.

[73] Assignee: Life Resuscitation Technologies, Inc., Chicago, Ill.

[21] Appl. No.: 568,462

[22] Filed: Dec. 7, 1995

[51] Int. Cl.⁶ .......................... A61K 31/70; A61K 31/40
[52] U.S. Cl. ............................... 514/419; 514/913
[58] Field of Search ..................... 514/419, 913

[56] References Cited

U.S. PATENT DOCUMENTS

| | | | |
|---|---|---|---|
| 4,654,361 | 3/1987 | Samples | 514/419 |
| 4,687,763 | 8/1987 | Wurtman | 514/53 |
| 5,149,321 | 9/1992 | Klatz et al. | 604/52 |

OTHER PUBLICATIONS

E. L. Cerchiari et al., "Effects of Combined Superoxide Dismutase and Deferoxamine on Recovery of Brainstem Auditory Evoked Potentials and EEG After Asphyxial Cardiac Arrest in Dogs", *Resuscitation*, vol. 19, pp. 25–40, (1990).

Y. Leonov et al., "Hypertension With Hemodilution Prevents Multifocal Cerebral Hypoperfusion After Cardiac Arrest in Dogs", *Stroke*, vol. 23, No. 1, pp. 45–53, (1992).

P. Giusti et al., "Melatonin Protects Primary Cultures of Cerebellar Granule Neurons from Kainate But Not From N–Methyl–D–Aspartate Excitotoxicity", *Experimental Neurology*, vol. 131, pp. 39–46, (1995).

M. Abe et al., "Inhibitory Effect of Melatonin on Cataract Formation in Newborn Rats: Evidence For an Antioxidative Role for Melatonin", *Journal of Pineal Research*, vol. 17, pp. 94–100, (1994).

D. Melchiorri et al., "Potent Protective Effect of Melatonin on In Vivo Paraquat–Induced Oxidative Damage in Rats", *Life Sciences*, vol. 56, No. 2, pp. 83–89, (1995).

E. A. Lane et al., "Pharmacokinetics of Melatonin in Man: First Pass Hepatic Metabolsm", *Journal of Clinical Endocrinology and Metabolism*, vol. 61, No. 6, pp. 1214–1216, (1985).

C.S. Shida et al., "High Melatonin Solubility in Aqueous Medium", *Journal of Pineal Research*, vol. 16, pp. 198–201, (1994).

P. Safar, M.D. et al., "Emergency Cardiopulmonary Bypass for Resuscitation from Prolonged Cardiac Arrest", *American Journal of Emergency Medicine*, vol. 8, No. 1, pp. 55–67, (1990).

R. Lavine et al., "Cardiopulmonary Bypass After Cardiac Arrest and Prolonged Closed–Chest CPR in Dogs", *Annals of Emergency Medicine*, vol. 16, No. 6, pp. 620–627, (1987).

J. L. Mosinger et al., "Blockade of Both NMDA and Non–NMDA Receptors is Required for Optimal Protection Against Ischemic Neuronal Degeneration in the In Vivo Adult Mammalian Retina", *Experimental Neurology*, vol. 113, pp. 10–17, (1991).

Dr. M. F. Beal, "Neuroprotective Effects of L–Kynurenine on Hypoxia–Ischemia and NMDA Lesions in Neonatal Rats", *Journal of Cerebral Blood Flow and Metabolism*, vol. 12, No. 3, pp. 400–407, (1992).

D. W. Marion, M.D. et al., "Resuscitative Hypothermia", *Critical Care Med.*, vol. 24, No. 2, pp. S81–S89, (1996).

B. Schmitz et al., "Resuscitation from Cardiac Arrest in Cats: Influence of Epinephrine Dosage on Brain Recovery", *Resuscitation*, vol. 30, pp. 251–262, (1995).

S. P. Woodhouse et al., "High Dose and Standard Dose Adrenaline Do Not Alter Survival, Compared with Placebo, In Cardiac Arrest", *Resuscitation*, vol. 30, pp. 243–249, (1995).

F. Xiao et al., "Peritoneal Cooling for Mild Cerebral Hypothermia After Cardiac Arrest in Dogs", *Resuscitation*, vol. 30, pp. 51–59, (1995).

C. F. Zwemer et al., "Hypoxic Cardiopulmonary–Cerebral Resuscitation Fails to Improve Neurological Outcome Following Cardiac Arrest in Dogs", *Resuscitation*, vol. 29, pp. 225–236, (1995).

K. Kuboyama et al., "Delay in Cooling Negates the Beneficial Effect of Mild Resuscitative Cerebral Hypothemeria After Cardiac Arrest in Dogs: A prospective, Randomized Study", *Critical Care Medicine*, vol. 22, No. 9, pp. 1348–1358, (1993).

P.A. Vitte et al., "Plasma, Cerebrospinal Fluid, and Brain Distribution of ¹⁴C–Melatonin in Rat: A Biochemical and Autoradiographic Study", *Journal of Pineal Research*, vol. 5, pp. 437–453, (1988).

S. Tisherman et al., "Resuscitation of Dogs from Cold–Water Submersion Using Cardiopulmonary Bypass", *Annals of Emergency Medicine*, vol. 14, No. 5, pp. 389–396, (1985).

*Primary Examiner*—C. Warren Ivy
*Assistant Examiner*—D. Margaret M. Mach
*Attorney, Agent, or Firm*—Oliff & Berridge

[57] ABSTRACT

A method for treating or preventing anoxic or ischemic brain injury that includes administering melatonin to a person who is suffering from or has a high risk of suffering from an anoxic or ischemic insult or injury. The method may also include administering complementary agents.

30 Claims, 3 Drawing Sheets

TREATMENT OR PREVENTION OF ANOXIC OR ISCHEMIC BRAIN INJURY WITH MELATONIN-CONTAINING COMPOSITIONS

FIELD OF THE INVENTION

The present invention relates generally to treating or preventing ischemic and anoxic brain injuries, particularly those associated with normothermic cardiac arrest. More particularly, the present invention provides a composition and method for resuscitation of the brain and maintenance of viability during or after trauma or other periods of decreased blood flow, allowing the health professional extra time to restore blood circulation and body functions.

BACKGROUND

Hundreds of thousands of people suffer from sudden cardiac arrest each year in the United States alone. During cardiac arrest, the heart ceases to pump blood. Subsequently, there is no circulation, and the brain fails to receive freshly oxygenated blood. Without a steady supply of oxygenated blood, the brain will cease to function.

Current resuscitation techniques for cardiac arrest victims have been directed almost exclusively towards the heart. However, even with methods such as cardiopulmonary resuscitation (CPR), patient survival rates are low. In hospitals and clinics with advanced CPR and advanced life support (ALS) systems, the survival rate is normally around 14%. Outside of hospital settings, the survival rate is about 5%. Among cardiac arrest victims overall, less than 10% survive neurologically intact and without significant brain damage. The other approximately 90% either die or sustain some neurologic injury from ischemia (i.e., lack of blood flow to the brain), or anoxia (i.e., lack of oxygen to the brain).

Such frequency of neurologic injury occurs in part because after cardiac arrest, basic cardiopulmonary resuscitation and advanced life support techniques, such as closed chest cardiac massage and electrical defibrillation, typically require fifteen to twenty minutes to restore circulation from a failed heart. Reversible neurologic damage begins as early as four minutes after circulation stops, and normally irreversible neurologic damage begins as early as five minutes after circulation stops. Countless research projects, patents, drugs, and clinical trials have been devoted to extending the reversible period of cardiac arrest in humans, but the long-established limit of five minutes of cardiac standstill remains unchanged. To combat this neurologic injury, initial resuscitation efforts need to be directed toward reviving the brain, not just to resuscitating the heart.

The short viability of brain tissue upon deprivation of oxygenated blood is a result of the requirement of high amounts of nutrients for tissue maintenance. Brain tissue uses almost all of the nutrients supplied by the circulating blood for maintenance and has very little remaining for storage. Absent blood flow to the brain, the small amount of stored nutrients is rapidly exhausted. Once exhausted, brain oxygen content rapidly depletes. This oxygen depletion is traumatic and causes a series of reactions in the oxygen-starved brain tissue cells. When blood flow is restored, the newly-delivered oxygen paradoxically produces a burst of oxidative damage (oxygen paradox), and calcium carried by the blood leaks into blood vessel smooth muscle cells, causing vasoconstriction (part of the reason for the so-called "no-reflow phenomenon"), and also leaks into brain cells, triggering a biochemical cascade culminating in further vascular obstruction and cell death. Certain neurotransmitters, particularly glutamate, are also released in excessive quantities. This results in damage from overstimulation, mediated largely by neurotransmitter-induced transport of calcium into neurons. This damage resulting from excessive release of excitatory neurotransmitters has been termed "excitotoxicity."

Prior efforts at resuscitating the brain have involved free radical inhibitors (Lazaroids), calcium channel blockers (lidoflazine, verapamil, etc.), barbiturate-induced comas, glutamate receptor blockade and a large assortment of other miscellaneous methods. The ultimate result of all of these pharmacological approaches, however, has been failure. Initially promising results have proven to be unreproducible, and results obtained in small animals (rats, hamsters, mice and gerbils) have proven to be inapplicable to dogs or humans. Recently, Lazaroids were shown to increase rather than decrease the mortality rate of human cardiac arrest survivors.

It has been learned that the treatment of stroke and the treatment of global cerebral ischemia are not the same. Furthermore, the treatment of cerebral hemorrhage is distinct from the treatment of global cerebral ischemia. Thus, agents such as streptokinase, iron chelators and superoxide dismutase are relatively ineffective for global cerebral ischemia. *Resuscitation* 19:25–40, 1990.

Safar et al. disclose several non-pharmacological variables that appear to be critical for the resuscitation of canine subjects after normothermic cardiac arrest of up to 11 minutes. (See Safar et al., "Improved Cerebral Resuscitation from Cardiac Arrest in Dogs with Mild Hypothermia plus Blood Flow Promotion", in press.) These variables are: a) systemic hypothermia to 34° C. induced as soon as possible after the onset of resuscitation and maintained for 12 hours thereafter; b) hemodilution to reduce blood viscosity to enhance cerebral tissue perfusion; and c) prompt restoration of mean arterial pressure (MAP) to superphysiological levels, e.g., an immediate brief bout to about 200 mm Hg upon the onset of resuscitation followed by a pressure of approximately 140 mm Hg for at least 4 hours thereafter.

Factors b) and c) above are referred to as "flow promotion" modalities and have been shown to preclude the otherwise inexorable "no reflow phenomenon" (see Leonov et al., *Stroke* 23:45–53, 1992). The "no reflow phenomenon" is a phenomenon whereby cerebral perfusion deteriorates after about 30 minutes or so of attempted resuscitation.

The results in Safar et al. depend, as noted, on being able to create a hypertensive MAP immediately upon the onset of resuscitation and to sustain a high MAP for several hours thereafter. For example, when mild hypothermia was combined with flow promotion, the neurological deficit score (NDS) and the histological damage score (HDS) were 8±9% and 43±9% (HDS range, 32–56), respectively. In comparison, when flow promotion was omitted, NDS soared to 27±19%, and HDS rose to 81±13% (HDS range, 70–104). *Crit. Care Med.* 21: 1348–1358, 1993.

Unfortunately, it is far from clear that hypertensive reflow conditions will always be feasible in a person who has experienced a spontaneous cardiac arrest. A heart attack usually occurs due to some underlying insult to the heart, such as an infarct or vasospasm related to atherosclerosis. In aged populations, which are the populations most at risk of cardiac arrest, additional conditions such as congestive heart failure, etc., may coexist with the condition that led to cardiac arrest. Furthermore, soldiers who suffer cardiac arrest in battlefield conditions frequently do so because of excessive blood loss. Any of these or other insults existing prior to cardiac arrest may limit cardiac performance upon attempted resuscitation to the extent that MAP cannot be elevated to the requisite hypertensive range. In fact, even in presumably healthy dogs, achieving hypertensive or even normotensive MAPs after restoration of spontaneous circulation (ROSC) (resumption of heartbeat) is exceptionally difficult. In our experience, heart-lung machines have great difficulty in delivering flows that are capable of elevating systemic pressure (MAP) even to normotensive levels, and provide only minimal support of pressure once spontaneous circulation has been restored.

U.S. Pat. No. 5,149,321 is directed to a method and a brain resuscitation device that can provide a temporary answer to this problem. The method includes establishing an artificial circulation by catheterizing the circulatory system in both external carotid arteries, to deliver essential treatment components to the brain in a synthetic brain resuscitation solution. By instilling perfusate directly into the carotid arteries, the brain resuscitation device allows sufficient flow to be directed to the brain to achieve the initial pressures and temperatures called for in Safar et al., regardless of cardiac condition, while also delivering hemodilution and cerebroprotective medications.

This approach provides a critical window of opportunity. However, hypertensive support would still have to follow use of the device to meet the guidelines of Safar et al. This could be not only be difficult to achieve, but also hazardous in that hypertension could lead to bursting of fragile blood vessels.

Thus, the ability to eliminate the need for hypertensive support would be desirable or even essential for widespread successful treatment of prolonged cardiac arrest. Clearly, a resuscitation technology that is fully effective despite sustained normotensive or even mildly hypotensive MAPs post-ROSC would be of great value. Reliable means of accomplishing this goal in man or canines are not known.

An important agent used in the present invention is melatonin. Melatonin is used primarily to facilitate sleep and adjust for jet lag. Recently, it has become popular as a possible anti-aging substance involved in the so-called aging clock. It appears to regulate and integrate a variety of biological rhythms.

Melatonin was used in a tissue culture system involving cerebellar granule neurons. The experiment found that melatonin did not block glutamate-induced excitotoxicity. *Exp. Neurol.* 131: 39–46, 1995.

Further, melatonin has been shown recently to be a good antioxidant in non-cerebral tissues when given in massive doses, such as 4 mg/kg to 10 mg/kg. *J. Pineal Res.* 17: 94–100, 1994, and *Life Sci.* 56: 83–89, 1994. Melatonin has also been shown to penetrate the blood brain barrier rapidly. *J. Pineal Res.* 5: 437–53, 1988. However, melatonin has not previously been used as a cerebroprotective agent for patients or experimental animals following prolonged cardiac arrest.

Other antioxidants, such as dimethylthiourea, which is also a highly penetrative antioxidant, have not proven useful in the treatment of postischemic cerebral ischemia. In addition, the only putative antioxidant ever tried in human clinical trials, tirilazad, has proven ineffective. In general, despite intensive investigation, antioxidants have not been shown to reverse cognitive impairment in man or in dogs when given after a profound ischemic insult.

Another problem in cerebral resuscitation is the unpredictability of cardiac arrest. Many people experience cardiac arrest without warning. Most drugs found in animal experiments to be protective against ischemia when used as pretreatments do not work when given after rather than before the ischemic insult. Clearly, a therapy that can reverse brain damage when given only after an ischemic insult would be of great value.

SUMMARY OF THE INVENTION

It is therefore an object of this invention to provide treatment or prophylaxis of ischemic and anoxic brain injuries during or immediately after the period of cardiac arrest whereby resuscitation efforts can be applied after more extended times than in the prior art so as to allow a patient to survive neurologically intact.

It is also an object of the invention to provide a method of treatment or prophylaxis of ischemic and anoxic brain injuries upon cardiac arrest so as to avoid the "no reflow phenomenon," whereby cerebral perfusion deteriorates after a period of time of attempted resuscitation.

It is a further object of the invention to provide a method of treatment or prophylaxis of ischemic and anoxic brain injuries upon cardiac arrest without immediate hypertensive reflow conditions.

It is yet another object of the invention to prevent and reverse potential damage to the brain and associated neurologic tissue suffered as a result of ischemic injury due to such traumas as, for example, cardiac arrest, major trauma, suffocation, drowning, electrocution, blood loss, extreme hypotension, shock and poisoning from substances including carbon monoxide and cyanide.

These and other objects are achieved by the use of a novel cerebroprotective agent and useful adjunctive agents when given even after eleven or more minutes of normothermic cardiac arrest. In particular, the present invention is directed to a method of treatment or prophylaxis of ischemic and anoxic brain injuries by administering melatonin to a person suffering from an ischemic or anoxic insult. The present invention is also directed to a method of pretreating a person at high risk for suffering from an ischemic or anoxic insult. Further, the present invention is directed to compositions comprising melatonin that can be used in methods of the present invention. The present invention may also be used for veterinary purposes.

BRIEF DESCRIPTION OF THE DRAWINGS

FIG. 2 in part A shows the blood pressure of a canine subjected to 11 min of cardiac arrest followed by treatment with the protocol of Example II.

FIG. 2 in part B shows the tympanic, rectal, and esophageal temperatures of a canine subjected to 11 min of cardiac arrest followed by treatment with the protocol of Example II.

DETAILED DESCRIPTION OF PREFERRED EMBODIMENTS

In an embodiment of the present invention, melatonin is delivered to a mammal such as a human, dog or horse suffering from an anoxic or ischemic injury. For the purposes of this application, a "mammal suffering from an ischemic or anoxic insult" includes a mammal that has had an ischemic or anoxic insult in the last thirty minutes even if blood and oxygen circulation has been subsequently restored.

For the purpose of this application, an "ischemic or anoxic insult" is a trauma that causes a lack of blood flow to the brain and/or a lack of oxygen to the brain. Ischemic or anoxic insults include, but are not limited to, cardiac arrest, stroke, sickle cell crisis, infarction, claudication, suffocation, drowning, electrocution, blood loss, extreme hypotension, shock and poisoning from substances including carbon monoxide and cyanide. The present invention is particularly directed to treating ischemic or anoxic states that arise from cardiac arrest.

In an embodiment of the present invention, the melatonin is administered during the ischemic or anoxic insult, during the restoration of circulation or reoxygenation, or immediately after circulation has been restored, either by ROSC or by, for example, cardiac bypass or use of the brain resuscitation device. Melatonin may be delivered by any means known to one of ordinary skill in the art including, but not limited to, oral, intramuscular, intraperitoneal, intravascular and subcutaneous administration.

In a preferred embodiment of the present invention, melatonin is delivered via an intravascular route to ensure that it reaches the brain as soon as possible after recirculation begins. More preferably, the melatonin is delivered intra-arterially, wherein one preferred intra-arterial route is via at least one carotid artery.

Melatonin is effective even when administered only in the immediate resuscitative period. However, in a preferred embodiment of the present invention, the administration of melatonin is continued for at least four hours after circulation resumes. Administration of melatonin may also be continued for up to twelve to twenty-four or more hours after circulation resumes. The administration of melatonin during this period may be either continuous or periodic.

Melatonin may be delivered in any effective amount. In a preferred embodiment of the present invention, 0.0001–5 mg of melatonin is delivered per kilogram of the patient in the immediate resuscitative period. In a more preferred embodiment of the present invention, 0.001–2 mg/kg melatonin is delivered. In an even more preferred embodiment, 0.1 to 2 mg/kg melatonin is delivered. If melatonin must be given intravenously rather than intra-arterially, these acute total doses may be adjusted moderately for clearance in the liver. See *J. Clin. Endocrinol. Metab.* 61: 1214–6, 1985. After the immediate resuscitative period, the maintenance dose of melatonin, given by, for example, slow IV drip, is preferably 0–0.1 mg/kg/hr.

Melatonin may be administered in any acceptable carrier. The carrier is selected based on the route of administration. Suitable carriers include, but are not limited to, water (e.g., for oral use prophylactically); saline (e.g., for slow IV drip for maintenance or for intramuscular, intraperitoneal, or subcutaneous use); aqueous perfusates (e.g., for acute use during initial reflow); emulsions including, for example, vitamin E micellized with suitable surfactants, high density lipoproteins or fish oil emulsions (e.g., for acute intravascular delivery of higher doses or for intraperitoneal instillation to provide a long-lasting depot for slow release of melatonin over prolonged periods); dimethyl sulfoxide (DMSO), such as 50% DMSO containing 0.9% w/v sodium chloride (e.g., when high concentrations of melatonin must be given in small volumes by IV push); or perfluorocarbon, such as Perflubron® (e.g., when hemodilution is not intended to reduce oxygen delivery to the brain).

Melatonin may be directly dissolved in an aqueous vehicle. Melatonin is soluble up to about 5 mM (1,162 mg/liter) in aqueous solution. *J. Pineal Res.* 16: 198–201, 1994. At this solubility, and with hemodilution to a hematocrit of about 25 from an initial value of 40, roughly 14 mg/kg patient can be administered. This dose is well above the dose that is required for practicing the invention as described herein.

Pure DMSO has been used to dissolve melatonin, but pure DMSO has a number of undesirable effects, including the ability to dissolve commercially-available plastics used in cardiopulmonary bypass circuits, which could be used as field units deployed to deliver perfusate intravascularly under emergency conditions.

Alternatively, melatonin may be dissolved in a suitable hydrophobic phase that is stably emulsified in an aqueous phase and can be diluted with the aqueous vehicle and remain suspended in solution. For example, the hydrophobic phase may be a micellized vitamin E emulsion, such as alpha d-tocopherol emulsion. One effective Vitamin E emulsion is a commercially-available product known as Vital-E and sold by Schering Plough (Kenilworth, N.J.). The mixture of melatonin and a suitable micellized form of vitamin E is referred to herein as "melan-E". In melan-E, the solubilizing medium is itself potentially protective.

In screening tests, it was shown that melan-E made with Vital-E is adequately tolerated, although Vital-E appeared to be an emetic and induced intestinal and bladder voiding and may be less desirable for use in a conscious patient. However, there is little or no increase in emesis or voiding with increasing melatonin dose in this vehicle. Circulating liver enzymes were minimally elevated.

An alternative vitamin E emulsion is commercially available that involves glycerol-ricinoleate as the emulsifying agent (a product known as Mycelized Vitamin E and sold by Metagenics, San Clemente, Calif.). This translucent emulsion did not produce emesis or voiding when used to solubilize and deliver 50 mg of melatonin. However, this alternative emulsion contains vitamin E as the acetate or succinate forms, which lack immediate vitamin E activity. The most preferred form of melan-E, consisting of alpha d-tocopherol emulsified with a non-emetic, non-laxative agent such as glycerol-ricinoleate, is not commercially available but can be easily prepared. Further, micellized preparations of other lipid-soluble antioxidants, such as coenzyme $Q_{10}$ dissolved in cardiolipin or in Perflubron® may be used in place of vitamin E.

Melatonin may be administered alone (either with a suitable carrier or, for oral prophylactic use, for example, as a pure powder) or in combination with additional protective agents. For example, melatonin may be delivered with one or more of the additional agents as an intravascular rescue solution or perfusate. Alternatively, the additional agents may be administered individually either in combination with the use of an intravascular rescue solution or in the absence of any unified intravascular rescue solution.

Preferably, the melatonin is delivered primarily in a perfusate in the acute resuscitation period. Perfusion allows for protective agents to be introduced prior to the termination of hypoxia and prior to normal blood reflow and thereby allows for protection before the onset of free radical, inflammatory, and excitotoxic processes triggered by reintroduction of oxygen and calcium, and allows for the removal of trapped cerebral blood with a low-viscosity, red cell-disaggregating perfusate. Further, in a preferred embodiment of the present invention, the perfusate has a lower temperature than blood. Thus, perfusion allows for rapid invasive cooling.

Preferably, the melatonin is administered with a hemodiluent. Suitable hemodiluents include those known to one of ordinary skill in the art, such as those taught in *Am. J.*

*Emerg. Med.* 8:55–67, 1990; *Ann. Emerg. Med.* 16:620–627, 1987; *Ann. Emerg. Med.* 14:389–396, 1985; *Acta Neurochir. Suppl.* (Vienna) 57:110–121, 1993; and *Stroke* 3:45–53, 1992, which are incorporated herein in their entirety by reference. A preferred class of hemodiluent is one containing Perflubron® perfluorocarbon (Alliance Pharmaceuticals, San Diego, Calif.), either oxygenated or deoxygenated.

In a preferred embodiment of the present invention, at least one of the following agents or a derivative thereof is administered to the brain in addition to melatonin: (1) kynurenine or kynurenic acid; (2) mannitol; and (3) dextran 40. Mannitol can be replaced with other impermeants such as sorbitol, raffinose, glucuronic acid, lactobionate, gluconate, or sucrose to control cell swelling. Kynurenine is equivalent in its effect to kynurenic acid, which is its active metabolite, and is interchangeable with kynurenic acid. Of the above agents, combining melatonin with kynurenine, kynurenic acid, or a derivative thereof is most preferred.

In a further embodiment of the present invention one or more of the following agents or derivatives thereof may also be administered with melatonin: a pH buffer, alpha-phenyl-N-tert-butyl nitrone (PBN), gammahydroxybutyrate (GHB) and Fructose 1,6-bisphosphate (FbP). Suitable pH buffers include, but are not limited to, tris(hydroxymethyl)-aminomethane (THAM), n-[2-hydroxyethyl]piperazine-n'-[2-ethane sulfonic acid](HEPES), histidine, phosphate, and piperazine-n,n'-bis[2-ethane sulfonic acid] (PIPES).

Preferably, the following amounts of the above agents per kilogram of the patient are used in the acute resuscitation period:

1. pH buffer: 0–5 mmol/kg, more preferably 0.1–2 mmol/kg, even more preferably 0.5–1 mmol/kg;
2. mannitol or its equivalent: 0–3.0 g/kg, more preferably 0.2–1.0 g/kg;
3. dextran 40: 0–5.0 g/kg, more preferably 2.0–3.0 g/kg;
4. PBN: 0–50 mg/kg, more preferably 1–20 mg/kg;
5. micellized vitamin E: 0–1000 IU/kg, more preferably 5–300 IU/kg;
6. kynurenine or kynurenic acid: 0–50 mg/kg, more preferably 1–20 mg/kg;
7. GHB: 0–1000 mg/kg, more preferably 0–400 mg/kg;
8. Fructose 1,6-bisphosphate (FbP): 0–1.0 g/kg, more preferably 0.05–0.2 g/kg.

Mannitol or its equivalent may be used to reverse cerebral swelling immediately upon initiating perfusion. THAM or another buffer may be used to reverse acidosis. Dextran 40 may be used in order to prevent or minimize red cell clumping.

PBN, kynurenine, and GHB may produce a hypotensive effect. Their doses can be titrated to minimize this effect to minimize the need for pressors and the likelihood of cardiovascular collapse. The combination of GHB and kynurenine is intended to block excitotoxicity and spare ATP. Kynurenine is a particularly strategic agent for blocking glutamate-mediated (both NMDA and kainate receptor specific) excitotoxicity. *Exp. Neurol.*, 113:10–17, 1991; *J. Cerebral Blood Flow Metab.*, 12:400–407, 1992. It is capable, in higher doses, of virtually abolishing cerebral electrical activity. GHB is an energy-sparing agent that induces natural sleep. Its well-known convulsive properties would normally contraindicate its use for cerebral resuscitation, but the simultaneous use of kynurenine prevents these convulsive side effects, allowing the energy-sparing benefits of GHB to be realized without deleterious consequences.

Melatonin, alpha d-tocopherol and PBN all function as antioxidants. However, only very limited success has been reported in conjunction with the use of the latter two agents by others. However, in combination with melatonin they provide backup protection that is generally helpful. Melatonin has other functions that go beyond its role as an antioxidant. It has an extraordinary ability to penetrate cells and organelles, it has receptors on the surfaces of many cells, it binds to DNA to protect it from damage, and it regulates most hormonal processes in the body. This integrative or orchestrative effect of melatonin may also be an important element of its beneficial actions.

In an embodiment of the present invention, a melatonin-containing perfusate is used to dilute the blood of a patient. Preferably, 30 to 100 ml of perfusate per kilogram of patient is used. More preferably, 40 to 80 ml of perfusate per kilogram of patient is used. In a preferred embodiment of the present invention, the perfusate dilutes the blood to a hemocrit of 25–35. In another embodiment of the present invention, the perfusate is used to replace blood. In this embodiment, the perfusate is administered by, for example, the apparatus disclosed in U.S. Pat. No. 5,149,321, which is incorporated herein in its entirety by reference.

In a further embodiment of the present invention, the blood pressure of the mammal is hypotensive or nomotensive for 1 to 3 hours or longer following resuscitation or for a substantial portion thereof.

When warning of the risk of an impending cardiac arrest is available, the application of the above therapeutic approach can be extended to the pre-arrest period. Melatonin may be administered for this purpose in doses totaling about 0.01 to 100 mg/day, preferably 0.1 to 50 mg/day, more preferably about 1 to 10 mg/day, for most adult human patients.

In addition, one or more of the optional agents described above may be administered with the melatonin prior to cardiac arrest. PBN and kynurenine or kynurenic acid may be administered in doses totalling about 0.1 to 20 mg or, more preferably, 1 to 20 mg, of either drug per patient per day. In addition, vitamin E (alpha d-tocopherol) at, for example, 50–800 IU/day, and/or coenzyme $Q_{10}$ at, for example, 30–300 mg/day may also be administered. Melatonin, kynurenine, and PBN should each be administered at doses that do not impair normal mental or other function so that the patient's life can proceed normally despite protection against effects of a future heart attack or other anoxic or ischemic insult. Neither vitamin E nor coenzyme $Q_{10}$ produce any subjectively noticeable effects in the pretreatment dose ranges specified.

Pretreatment with melatonin may augment the effectiveness of post-ischemic treatment. In many instances, particularly since melatonin is entirely nontoxic when given via the oral route, pretreatment will be feasible. Examples include pretreatment of soldiers prior to combat, pretreatment of patients in intensive care units or surgery patients who are at risk for cardiac arrest and/or stroke, pretreatment of previous heart attack and/or stroke victims who are living at home and pretreatment of other individuals at high risk for anoxic or ischemic insult, such as those having an occurrence of atherosclerosis or vascular stenosis or those inheriting sickle cell trait or those having a physically hazardous occupation, such as prize fighters, race car drivers, or divers. A further example is pretreatment prior to elective deep whole-body hypothermia and total body washout for circulatory arrest for the correction of aneurysms or other defects, a procedure which imposes ischemia and potential hypoxia while washing most endogenous body stores of melatonin out of the body, thus heightening its vulnerability.

In a further embodiment of the present invention, the therapeutic approach of the invention may be used in the treatment of massive traumatic injury involving the need for immediate profound hypothermia to permit surgical repair of vascular wounds prior to attempting resuscitation. In this embodiment, the patient will be cooled with a perfusate intended to locally or globally completely replace blood for as long as several hours of deep hypothermic transport and/or hypothermic surgery. Melatonin and optionally one or more of the agents described above, including PBN, kynurenine or kynurenic acid, FbP, and GHB, can be included in the hypothermic perfusate so that the agents will already be in the patient when resuscitation is attempted. As the perfusate is replaced with blood and the patient is rewarmed, administration of these medications is preferably continued so as to produce the same effect as described above for the acute cardiac arrest situation.

In a preferred embodiment of the present invention, the patient (assumed to be an adult) is pretreated, when feasible, with 3–6 mg of melatonin (for example, at bedtime), 120 mg of coenzyme $Q_{10}$ (for example, in the morning), and 3 doses (for example, in the morning, afternoon and evening) of 200 IU of vitamin E each. When cardiac arrest occurs, and if help does not arrive until at least 4 to 6 minutes have elapsed, the patient is immediately perfused intra-arterially with about 50 ml per kg patient of a perfusate that is precooled to 27°–32° C. and that contains, per liter, melatonin (30–40 mg), kynurenic acid (150–200 mg), THAM (15–25 mmoles), mannitol (10–15 grams), PBN (300–350 mg), dextran 40 (40–60 grams), micellized alpha d-tocopherol (150–250 IU), fructose 1,6-bisphosphate (0.5–1.5 grams), sodium chloride (6–10 grams), potassium chloride (3–6 mmoles), magnesium sulfate (2–5 mmoles), and heparin (500–2000 units) and whose pH has been set to 7.3 to 8.0. Effluent blood from the patient is allowed to displace the extracorporeal perfusate volume but is returned to the patient within 60 to 180 min of the beginning of resuscitation. Perfusate/blood mixture is recirculated to maintain blood pressure above 30 to 50 mmHg prior to ROSC and to cool the patient to 33.5° to 34.5° C. and to initially maintain that temperature. GHB, 100–300 mg/kg, is given at 10 and 20 min after initiating perfusion. Perfusate/blood mixture is oxygenated starting at 0–2 min after the onset of perfusion. After ROSC (via electrical defibrillation or other means) pressors are used to bring MAP to 90±10 mmHg, preferably by direct delivery of pressors to the heart rather than by intravenous (peripheral) administration. IV maintenance infusions of FbP (1–3 g/hr), melatonin (100–1000 micrograms/hr) and kynurenic acid (50–200 mg/hr) are begun. Temperature is maintained at 34±0.5° C. for 12–15 hours, then warming is permitted to occur. If warming leads to seizure activity, the seizure activity is treated with kynurenic acid and the patient is re-cooled to 34° C. for another 6–12 hours before rewarming is reattempted. This process is repeated until seizure activity is no longer observed on warming. Medical management in other respects should be according to the best prevailing established procedures.

The specific rescue protocol described above and in the examples below includes both the individual pharmaceutical agents used and the method by which they are used. The exact staging of agent introduction as described, however, is not mandatory. Embodiments of the present invention vary from rescue protocols that contain minor variations in the timing of agent administration described below to the inclusion of all agents in the initial cerebral resuscitation perfusate to the intravenous use of the rescue agents during ordinary CPR when direct invasive introduction is impossible.

In a preferred embodiment, the treatment is multifaceted, involving hypothermia, hemodilution with a supportive perfusate that is instilled directly into the vascular system, preferably intra-arterially, and the use of a composition described herein.

EXAMPLE I

A 24 kg canine subject was premedicated with agents used to prevent superfluous (gastric) damage, i.e., 30 cc of Maalox, cimetidine (150 mg, IM) and misoprostol (50 mcg per os) about 2 hours before being anesthetized. Preparation for anesthesia included administration of atropine (0.4 mg, IM) and acepromazine (IM, as a sedative) within 30 minutes before anesthesia. Anesthesia was accomplished with standard doses of sodium pentobarbital IV, after which the animal was intubated and mechanically ventilated. 9.4 mg of metubine were administered to inhibit shivering.

The bypass circuit was primed with a solution consisting of 0.7 liter of a commercially-available IV solution (Normosol-R, pH 7.4) and 0.7 liter of commercially available 10% w/v dextran 40 in normal saline to which were added 20 grams (100 ml of a 20% w/v sterile IV solution) of mannitol, 500 milligrams of alpha-phenyl-N-tert-butyl nitrone (PBN) (previously dissolved in 40 cc of normal saline), and 50 ml of 0.6 M tris(hydroxymethyl)-aminomethane (THAM). Thus, about 1.5 liters of this rescue solution were available and were used as an arterial perfusate to cool and hemodilute the dog upon initiation of bypass.

The solution was initially precooled to about room temperature prior to the onset of cardiac arrest so that direct invasive cooling could be initiated after precisely 11 minutes of arrest time. Precooling to this extent, however, was found to produce a considerable temperature undershoot (see below), and an initial temperature of 28°–34° C. is presently preferred when the target temperature of the subject is 33°–34° C.

Cardiac arrest was instituted by applying 60 cycle, 110 V current via two long needles placed into the thoracic wall on either side of the heart and parallel to the thoracic wall. Cardiac arrest was verified by EKG and arterial blood pressure. Cardiac arrest was allowed to continue for 11 minutes. No treatment was administered to the animal during this time, and no attempt was made to cool the animal during this time. The resumption of spontaneous heartbeat was attempted approximately 1–2 min after initiation of cardiopulmonary bypass and was instituted by using a standard defibrillator. Defibrillation was accomplished in one attempt.

As soon as venous blood began reaching the bypass reservoir, 40 IU/kg of micellized alpha d-tocopherol (Vital-E, manufactured by Schering-Plough; 3.2 ml of the 300 IU/ml material) containing 10 mg of pre-dissolved melatonin diluted with normal saline to a final volume of 10 ml of melan-E were added to the reservoir, and an additional 40 ml of melan-E were similarly administered over the ensuing 7 minutes or so. The melan-E is diluted in order to produce a low enough viscosity to allow filter sterilization through a 0.22 micron syringe filter. The dog's temperature was brought to below 34° C. within about 4 minutes. At 8, 11, and 13 min of resuscitation, 3.5 mg/kg (each in 20 cc normal saline) of kynurenine were added into the bypass reservoir, and at 10 and 20 minutes following the end of the 11 minute formal arrest time (defined as the time during which the MAP was at or below 30 mmHg), 3 grams (125 mg/kg) of gammahydroxybutyrate (GHB) were added in the same way.

Thus, the total doses administered per kilogram of the dog were approximately:

1. hemodiluent, 60 ml/kg;
2. pH buffer (THAM), 1.25 mmoles/kg
3. mannitol, 0.83 g/kg;
4. dextran 40, 2.9 g/kg;
5. PBN, 21 mg/kg;
6. micellized vitamin E, 200 IU/kg;
7. melatonin, 2.1 mg/kg;
8. kynurenine, 10.5 mg/kg; and
9. GHB, 250 mg/kg.

Hypothermia was maintained for approximately 13–15 hours after the onset of resuscitation. Metubine iodide was used to prevent shivering and uncontrolled ventilation during this time, after which body temperature was allowed to drift slowly upward.

Figure 1:
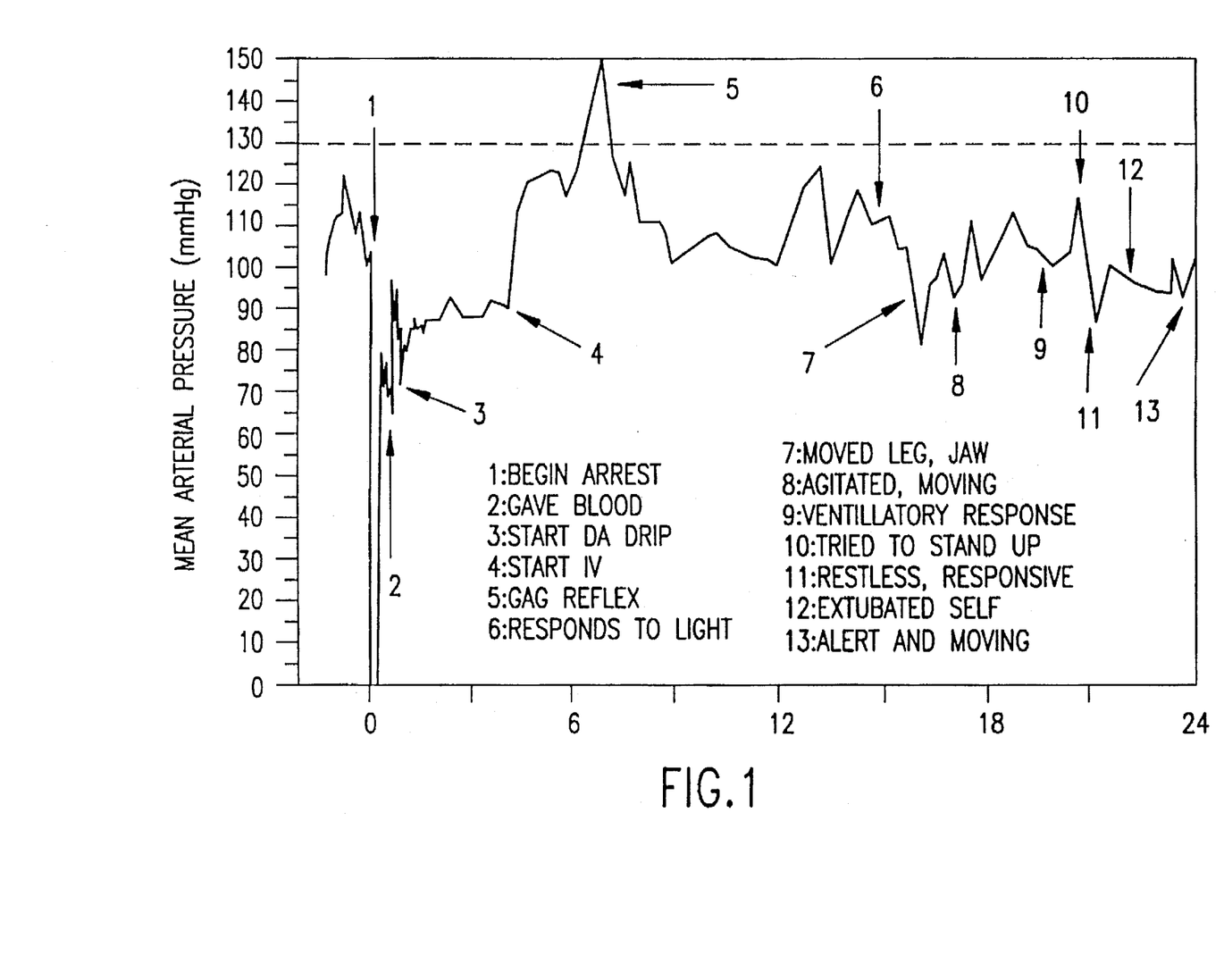
FIG. 1 shows the blood pressure of a canine subjected to 11 minutes of cardiac arrest followed by treatment with the protocol of Example I.

The post-arrest MAP history is shown in FIG. 1. In Example I, MAP remained below 90 mmHg for approximately 4 hours post-insult, and subsequently rose above Leonov's (Stroke 23:45–53, 1992) minimum 130 mmHg target value only momentarily on one occasion.

The time course of neurological recovery over the first 24 hours is also charted in FIG. 1. As noted above, the large body of experience accumulated in the Safar laboratory and elsewhere has shown that canine subjects exposed to 11 minutes of cardiac arrest and allowed to remain hypotensive to the extent shown in FIG. 1 do not recover neurologically, but instead progress to a state of profound neurological impairment or permanent coma or death. However, in the present Example, neurological recovery appeared to be complete in the canine subject.

EXAMPLE II

The same protocol as in Example I was used on a second canine subject, except that kynurenine was given at 9, 12 and 15 minutes after starting resuscitation and GHB was given at 12 and 27 minutes following the end of the formal arrest period.

Figure 2A:
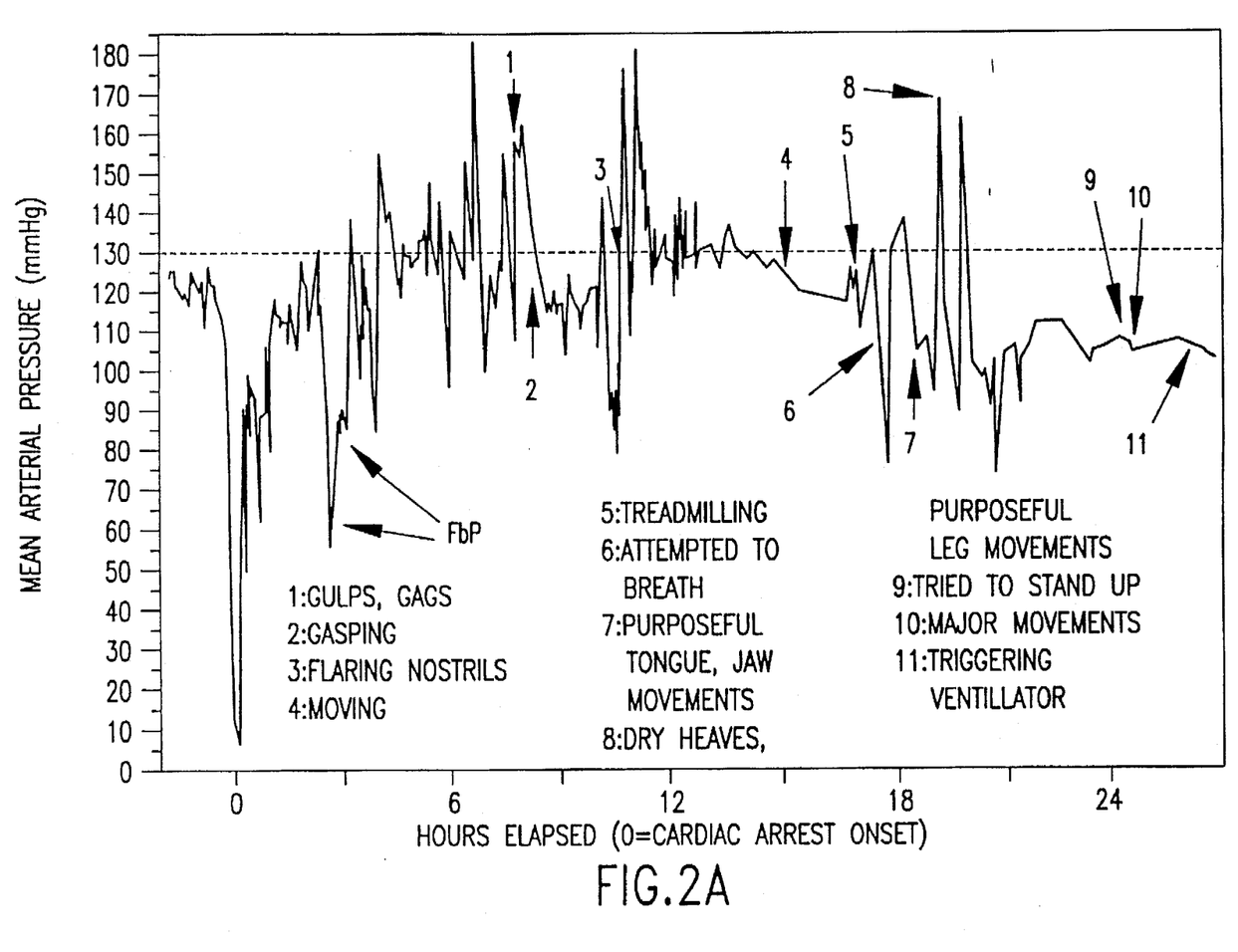

The post-arrest MAP history for this subject is shown in FIG. 2A. In Example II, MAP remained below 90–100 mmHg for about an hour, then gradually rose to 130 mmHg after a total of 3 hours of blood reflow, at which point cardiovascular collapse occurred, taking the MAP to below 60 mmHg. Although the cardiovascular collapse was reversed with fructose 1,6-bisphosphate (first 1 gram, then 2 grams, both by IV push), the target pressure of 130 mmHg was finally achieved stably only after a total of over 3 hours of resuscitation.

The time course of neurological recovery for the second subject over the first 27 hours is also charted in FIG. 2A. Although the canine subject was exposed to 11 minutes of cardiac arrest at 37.5° C. or above and allowed to remain hypotensive to the extent shown in FIG. 2A, neurological recovery appeared to be complete in the canine subject.

Figure 2B:
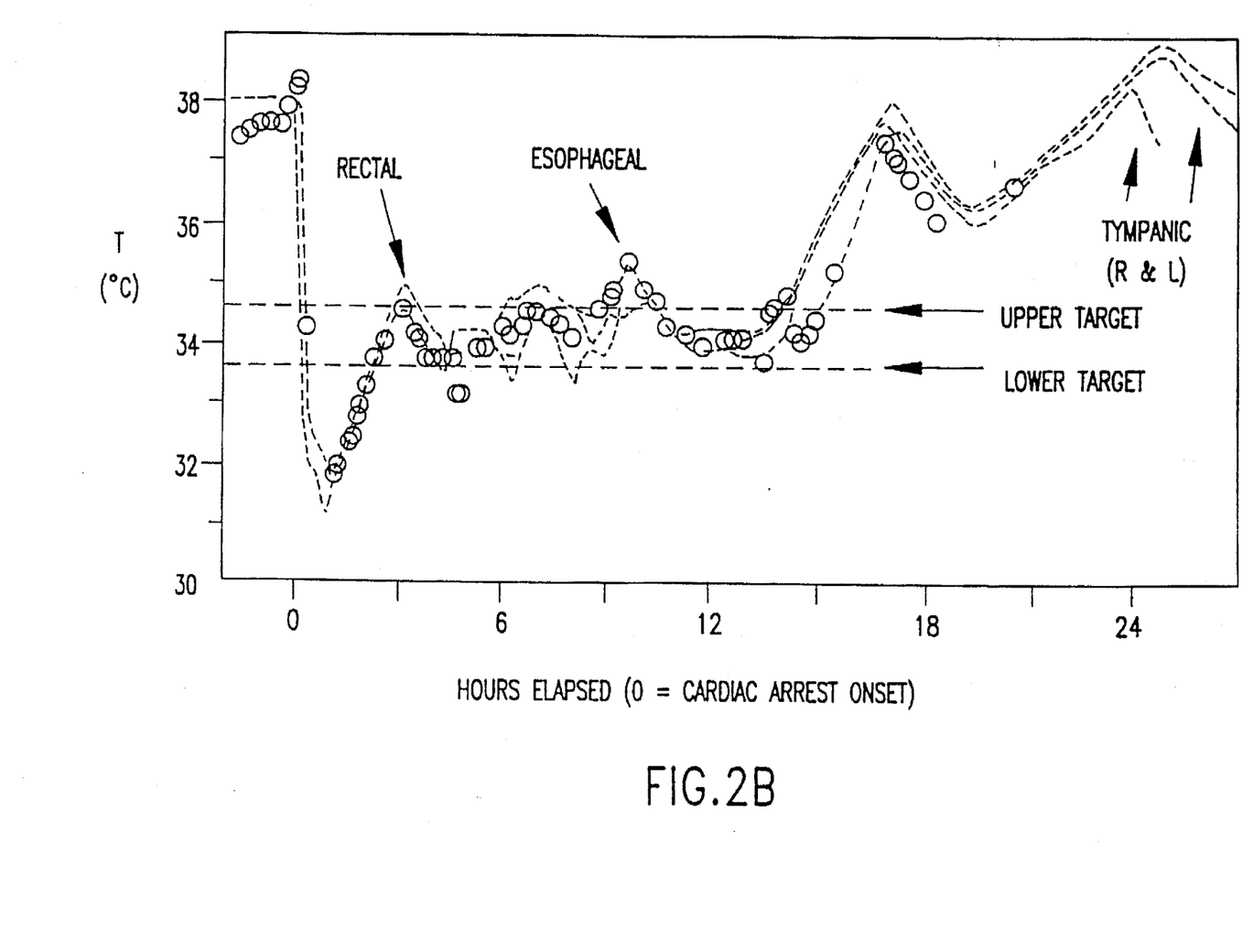

The thermal history of the second canine subject is shown in FIG. 2B. Our temperature undershoot was similar to the undershoots observed by Safar's group both in magnitude and in duration. The agreement between rectal, esophageal, and left (L) and right (R) tympanic membrane temperatures was virtually exact for the first 6 hours, after which the tympanic membrane probes became loose and varied from each other to some extent.

The foregoing embodiments are intended to illustrate and not limit the present invention. It will be apparent that various modifications can be made without departing from the spirit and scope of the invention as defined in the appended claims.

What is claimed is:

1. A method for treating or minimizing anoxic or ischemic brain injuries, comprising administering melatonin to a mammal suffering from an anoxic or ischemic insult.

2. The method of claim 1, wherein the mammal is a human.

3. The method of claim 1, wherein the melatonin is administered intravascularly.

4. The method of claim 3, wherein the melatonin is administered intra-arterially.

5. The method of claim 1, wherein the melatonin is administered within eleven minutes of the anoxic or ischemic insult.

6. The method of claim 1, wherein the anoxic or ischemic insult is caused by cardiac arrest.

7. The method of claim 1, wherein the melatonin is administered for a period of at least twelve hours.

8. The method of claim 1, wherein 0.0001 to 5 mg of melatonin is administered per kilogram of the mammal.

9. The method of claim 1, further comprising administering to said mammal at least one agent selected from the group consisting of a pH buffer, mannitol, dextran 40, PBN, micellized vitamin E, kynurenine, kynurenic acid, GHB, fructose 1,6-bisphosphate, coenzyme $Q_{10}$, perfluorocarbon, cardiolipin, and derivatives thereof.

10. The method of claim 1, further comprising administering kynurenine or kynurenic acid or a derivative thereof to said mammal.

11. The method of claim 1, wherein the melatonin is administered in a perfusate.

12. The method of claim 11, wherein the perfusate dilutes the blood to a hematocrit of 25–35.

13. The method of claim 11, wherein the perfusate replaces the blood.

14. The method of claim 1, wherein blood pressure of the mammal is hypotensive or normotensive for at least one hour following resuscitation.

15. A composition for the treatment or prophylaxis of anoxic or ischemic brain injuries, comprising melatonin and at least one agent selected from the group consisting of dextran 40, PBN, micellized vitamin E, kynurenine, kynurenic acid, GHB, fructose, 1,6-bisphosphate, coenzyme $Q_{10}$, perfluorocarbon,-cardiolipin, and derivatives thereof.

16. The composition of claim 15, wherein the melatonin is dissolved in micellized vitamin E.

17. The composition of claim 15, wherein the at least one agent is kynurenine, kynurenic acid, or a derivative thereof.

18. A method for preventing or minimizing permanent neurological damage resulting from anoxic or ischemic injury, comprising administering an effective amount of melatonin to a mammal at high risk of an anoxic or ischemic insult.

19. The method of claim 18, wherein the high risk results from an event selected from the group consisting of combat, surgery, occurrence of previous heart attack or stroke, occurrence of atherosclerosis or vascular stenosis, inheritance of sickle cell trait, or a physically hazardous occupation.

20. The method of claim 18, wherein the high risk results from a history of at least one of cardiac arrest or stroke.

21. A composition for treating ischemic or anoxic injury comprising melatonin, mannitol dextran 40 and at least one of kynurenic acid and kynurenine.

22. The composition of claim 21, further comprising a micellized vitamin E.

23. The composition of claim 22, further comprising GHB.

24. The composition of claim 23, further comprising a pH buffer.

25. The composition of claim 21, further comprising a perfluorocarbon or cardiolipin emulsion.

26. The composition of claim 22, further comprising a perfluorocarbon or cardiolipin emulsion.

27. The composition of claim 15, further comprising mannitol.

28. The composition of claim 15, wherein said composition is a perfusate.

29. A composition for the treatment or prophylaxis of anoxic or ischemic brain injuries, comprising melatonin, water and at least one agent selected from the group consisting of mannitol, dextran 40, PBN, micellized vitamin E, kynurenine, kynurenic acid, GHB, fructose 1,6-bisphosphate, coenzyme $Q_{10}$, perfluorocarbon, cardiolipin, and derivatives thereof.

30. The composition of claim 29, wherein said composition is a perfusate.

* * * * *